(12) United States Patent
Chance

(10) Patent No.: US 6,246,892 B1
(45) Date of Patent: *Jun. 12, 2001

(54) PHASE MODULATION SPECTROSCOPY

(75) Inventor: Britton Chance, Marathon, FL (US)

(73) Assignee: Non-Invasive Technology, Philadelphia, PA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/799,204

(22) Filed: Feb. 13, 1997

Related U.S. Application Data

(63) Continuation-in-part of application No. 08/731,443, filed on Oct. 15, 1996, now Pat. No. 6,134,460, which is a continuation of application No. 08/031,945, filed on Mar. 16, 1993, now Pat. No. 5,564,417, which is a continuation-in-part of application No. 08/076,370, filed on Jun. 14, 1993, now Pat. No. 5,553,614, which is a continuation of application No. 07/645,590, filed on Jan. 24, 1991, now abandoned.

(51) Int. Cl.$^7$ ....................................... A61B 5/00
(52) U.S. Cl. .................... 600/310; 600/407; 600/473; 600/476; 600/477
(58) Field of Search .................... 600/310, 314, 600/322, 343, 407, 473, 426, 422

(56) References Cited

U.S. PATENT DOCUMENTS

| 3,360,987 | 1/1968 | Flower et al. . |
| 3,365,717 | 1/1968 | Holscher . |

(List continued on next page.)

FOREIGN PATENT DOCUMENTS

| 156398 | 8/1982 | (DE) . |
| 55-141656A | 5/1980 | (JP) . |
| WO89/00281 | 1/1989 | (WO) . |
| WO92/20273 | 11/1992 | (WO) . |

OTHER PUBLICATIONS

Blumberg, W.E., *Biophys. J.*, 51:288 (Abstract) (1987).
Bonner, R.F. et al., *J. Opt. Soc. Am. Sec. A.*, 4:423–432 (1987).
Chance, "Rapid and Sensitive Apectrophotometry, I. The Accelerated and Stopped–Flow Methods for the Measurement of the Reaction Kinetics, etc.", *The Review of Scientific Instruments*, 22:619–638 (1951).
Chance, B., *Nature* (London), 169:215–230 (1952).
Chance, B., *Science.* 120:767–775 (1954).

(List continued on next page.)

*Primary Examiner*—David M. Shay
(74) *Attorney, Agent, or Firm*—Fish & Richardson, P.C.

(57) ABSTRACT

A spectroscopic system for quantifying in vivo concentration of an absorptive pigment in biological tissue includes an oscillator for generating a first carrier waveform of a first frequency on the order of $10^8$ Hz, a light source for generating light of at least two selected wavelengths modulated by the carrier waveform, and a detector for detecting radiation that has migrated over photon migration paths in the tissue from an input port to a detection port spaced several centimeters apart. At least one of the wavelengths is sensitive to concentration of an absorptive pigment present in the tissue, while the tissue exhibits similar scattering properties at the two wavelengths. A phase detector compares, at each wavelength, the detected radiation with the introduced radiation and determines therefrom the phase shift of the detected radiation at each wavelength. A processor quantifies the concentration of the absorptive pigment by employing the phase shifts measured at the two wavelengths and also employing a scattering property of the tissue.

67 Claims, 11 Drawing Sheets

U.S. PATENT DOCUMENTS

| | | |
|---|---|---|
| 3,522,992 | 8/1970 | Jaffe . |
| 3,638,640 | 2/1972 | Shaw . |
| 4,138,727 | 2/1979 | Mantz . |
| 4,223,680 | 9/1980 | Jobsis . |
| 4,281,645 | 8/1981 | Jobsis . |
| 4,321,930 | 3/1982 | Jobsis et al. . |
| 4,380,240 | 4/1983 | Jobsis et al. . |
| 4,458,694 | 7/1984 | Sollish et al. . |
| 4,510,938 | 4/1985 | Jobsis et al. . |
| 4,576,173 | 3/1986 | Parker et al. . |
| 4,714,341 | 12/1987 | Hamaguri et al. . |
| 4,795,256 | 1/1989 | Krause et al. . |
| 4,800,495 | 1/1989 | Smith . |
| 4,800,885 | 1/1989 | Johnson . |
| 4,805,623 | 2/1989 | Jobsis . |
| 4,807,630 | 2/1989 | Malinauskas . |
| 4,819,646 | 4/1989 | Cheung et al. . |
| 4,824,242 | 4/1989 | Frick et al. . |
| 4,827,934 | 5/1989 | Ekwall . |
| 4,827,938 | 5/1989 | Parker . |
| 4,832,484 | 5/1989 | Aoyagi et al. . |
| 4,846,183 | 7/1989 | Martin . |
| 4,863,265 | 9/1989 | Flower et al. . |
| 4,867,557 | 9/1989 | Takatani et al. . |
| 4,908,762 | 3/1990 | Suzuki et al. . |
| 5,119,815 | 6/1992 | Chance . |
| 5,122,974 | 6/1992 | Chance . |
| 5,167,230 | 12/1992 | Chance . |
| 5,187,672 | 2/1993 | Chance et al. . |
| 5,353,799 * | 10/1994 | Chance ............................ 600/476 |
| 5,402,778 * | 4/1995 | Chance ............................ 600/310 |
| 5,553,614 | 9/1996 | Chance . |
| 5,564,417 | 10/1996 | Chance . |
| 5,596,987 * | 1/1997 | Chance ............................ 600/473 |
| 5,664,574 * | 9/1997 | Chance ............................ 600/476 |
| 5,673,701 * | 10/1997 | Chance ............................ 600/473 |
| 5,779,631 * | 7/1998 | Chance ............................ 600/476 |
| 5,782,755 * | 7/1998 | Chance et al. .................... 600/473 |
| 5,792,051 * | 8/1998 | Chance ............................ 600/476 |
| 5,807,263 * | 9/1998 | Chance ............................ 600/473 |
| 5,820,558 * | 10/1998 | Chance ............................ 600/476 |
| 5,853,370 * | 12/1998 | Chance et al. .................... 600/476 |

OTHER PUBLICATIONS

Chance, B., *Biochemistry of Copper*, ed. Peisach, J. (Academic, New York), pp. 293–303.

Chance et al., "Time–Resolved Spectroscopy of Hemoglobin in Resting and Ischemic Muscle", *Analytical Biochem.*, 174:698–707 (1988).

Chance, B. et al., *Proc. Natl. Acad. Sci. USA*, 85:4971–4975 (1988).

Chance, B. et al., "Photon Migration in Muscle and Brain", *Photon Migration in Tissues*, Academic Press/New York (1989).

Cui et al., "Experimental Study of Migration Depth for the Photons Measured at Sample Surface", Proceedings of Time–Resolved Spectroscopy and Imaging of Tissues, SPIE, 1413:180–191 (1991).

Delpy, D.T., et al., "Estimation of optical pathlength through tissue from direct time of flight measurement", *Phys. Med. Biol.*, 33(12):1433–1442 (1988) (UK).

Duysens, L., *Pro. Biophys. Mol. Biol.*, 14:1–104 (1964).

Galeotti et al., (Eds.), *Membrane in Cancer Cells*, 551 N.Y. Acad. Sci. (1988) (preface).

Haida et al., "A Method to Estimate the Ration of Absorption Coefficients of Two Wavelengths Using Phase–Modulated Near Infrared Light Spectroscopy", *Analytical Biochemistry*, 208:348–351 (1993).

Jobsis–VanderVlient, F.F., *Adv. Exp. Med. Biol.*, 191:833–842 (1985).

Kaschke, et al., "Transillumination Imaging of Tissue by Phase Modulation Techniques", OSA Proceedings on Advances in Optical Imaging and PHoton Migration, 21:88–92 (1994).

Lakowicz, J.R., "Gigahertz Frequency–Domain Fluorometry: Resolution of Complex Intensity Decays, Picosecond Processes and Future Developments", Photon Migration in Tissues, Academic Press/NY, pp. 169–486 (1989).

Sevick et al., "Analysis of absorption, scattering, and hemoglobin saturation using phase modulation spectroscopy", Proceedings of Time–Resolved Spectroscopy and Imaging Tissues, SPIE, 1431:264–275 (1991).

Sevick et al., "Photon migration in a model of the head measured using time–and frequency–domain, etc.", Proceedings of Time–Resolved Spectroscopy and Imaging Tissues, SPIE, 1431:84–96 (1991).

Sevick et al., "Quantitation of Time–and Frequency–Resolved Optical Spectra for the Determination of Tissue Oxygenation", Analytical Biochemistry, 195:001–0022 (1991).

Van der Zee, et al., "Computed Point Spread Functions for Light in Tissue Using a Measured Volume Scattering Function," Advances in Experimental Medicine and Biology: Oxygen Transport to Tissue X, 222:191–197 (1988).

Weng et al., "Measurement of Biological Tissue Metabolism Using Phase Modulation Spectroscopic Technology", Proceedings of Time–Resolved Spectroscopy and Imaging of Tissues, SPIE, 1431:161–170 (1991).

* cited by examiner

PHASE MODULATION SPECTROSCOPY

CROSS REFERENCE TO RELATED APPLICATION

This application is a continuation-in-part of U.S. patent application Ser. No. 08/731,443, filed Oct. 15, 1996 now U.S. Pat. No. 6,134,460; which in turn is a continuation of U.S. patent application Ser. No. 08/031,945, filed Mar. 16, 1993, now U.S. Pat. No. 5,564,417; which in turn is a continuation-in-part of U.S. patent application Ser. No. 08/076,370, filed Jun. 14, 1993, now U.S. Pat. No. 5,553,614; which is a continuation of U.S. patent application Ser. No. 07/645,590, filed Jan. 24, 1991 now abandoned, all of which are incorporated by reference as if fully set forth herein.

BACKGROUND OF THE INVENTION

The present invention relates to quantitative analyses of absorptive constituents in biological tissues by employing a phase modulation spectroscopy.

Continuous wave (CW) tissue oximeters have been widely used to determine in vivo concentration of an optically absorbing pigment (e.g., hemoglobin, oxyhemoglobin) in biological tissue. The CW oximeters measure attenuation of continuous light in the tissue and evaluate the concentration based on the Beer Lambert equation or a modified Beer Lambert absorbance equation. The Beer Lambert equation (1) describes the relationship between the concentration of an absorbent constituent (C), the extinction coefficient ($\epsilon$), the photon migration pathlength <L>, and the attenuated light intensity ($I/I_0$).

$$\frac{\log[I/I_0]}{\langle L \rangle} = \sum \epsilon_i C_i \qquad (1)$$

The CW spectrophotometric techniques can not determine $\epsilon$, C, and <L> at the same time. If one could assume that the photon pathlength were constant and uniform throughout all subjects, direct quantitation of the constituent concentration (C) using CW oximeters would be possible.

In tissue, the optical migration pathlength varies with the size, structure, and physiology of the internal tissue examined by the CW oximeters. For example, in the brain, the gray and white matter and the structures thereof are different in various individuals. In addition, the photon migration pathlength itself is a function of the relative concentration of absorbing constituents. As a result, the pathlength through an organ with a high blood, hemoglobin concentration, for example, will be different from the same with a low blood hemoglobin concentration. Furthermore, the pathlength is frequently dependent upon the wavelength of the light since the absorption coefficient of many tissue constituents is wavelength dependent. Thus, where possible, it is advantageous to measure the pathlength directly when quantifying the hemoglobin concentration in tissue.

SUMMARY OF THE INVENTION

In general, in one aspect, a spectroscopic system for quantifying in vivo concentration of an absorptive pigment in biological tissue includes an oscillator constructed to generate a first carrier waveform of a first frequency on the order of $10^8$ Hz (i.e., in the range of 10 MHz to 1 GHz), a light source constructed to generate light of at least two selected wavelengths modulated by the carrier waveform, and a detector constructed to detect radiation that has migrated over photon migration paths in the tissue from an input port to a detection port spaced several centimeters apart. At least one of the wavelengths is sensitive to concentration of an absorptive pigment present in the tissue, while the tissue exhibits similar scattering properties at the two wavelengths. A phase detector is constructed to compare, at each wavelength, the detected radiation with the introduced radiation and determine therefrom the phase shift of the detected radiation at each wavelength. A processor is constructed to quantify the concentration of the absorptive pigment based on the phase shifts measured at the two wavelengths and based on a scattering property of the tissue.

In general, in another aspect, a spectroscopic system for quantifying in vivo concentration of an absorptive pigment in biological tissue includes an oscillator constructed to generate a first carrier waveform of a first frequency on the order of $10^8$ Hz (i.e., in the range of 10 MHz to 1 GHz), a light source constructed to generate light of at least two selected wavelengths modulated by the carrier waveform, and a detector constructed to detect radiation that has migrated over photon migration paths in the tissue from an input port to a detection port spaced several centimeters apart. At least one of the wavelengths is sensitive to concentration of an absorptive pigment present in the tissue, while the tissue exhibits similar scattering properties at the two wavelengths. The spectroscopic system also includes a phase splitter, two double balanced mixers, and a processor. The phase splitter is constructed to receive the carrier waveform and produce first and second reference phase signals of predefined substantially different phases. The first and second double balanced mixers are constructed to receive from the phase splitter the first and second reference phase signals, respectively, and also receive from the detector the detector signal to produce therefrom a real output signal and an imaginary output signal, respectively. The processor is constructed to receive a scattering property of the examined tissue and the real output signal and the imaginary output signal and quantify therefrom the concentration of the absorptive pigment in the examined tissue.

Different embodiments of this type of the spectrophotometer may include one or more of the following features. The processor may calculate, at each wavelength, a phase shift of the detected radiation as the inverse tangent of the ratio of the imaginary output signal and the real output signal. The processor may calculate, at each wavelength, a detected amplitude as the square root of the sum of the squares of the real output signal and the imaginary output signal.

In different embodiments, the spectrophotometer may be a dual wavelength, single frequency system or a dual wavelength, dual frequency system. Each system can measure data for a single source-detector separation (i.e., separation of the input port and the detection port) or for several source-detector separations.

Different embodiments of the spectrophotometer may include one or more of the following features.

The spectrophotometer may include a second oscillator constructed to generate a second carrier waveform of a second selected frequency on the order of $10^8$ Hz, while the tissue exhibits similar scattering properties at the selected frequencies. The source of the spectrophotometer is operatively coupled to the second oscillator and is constructed to generate electromagnetic radiation of the two wavelengths modulated by the second carrier waveform. The detector is further constructed to detect the radiation modulated by the second carrier waveform. The phase detector is further constructed to compare, at each the wavelength, the detected radiation of the second carrier waveform with the introduced radiation and determine therefrom the phase shift of the detected radiation of the second frequency.

The processor may calculate a ratio of absorption coefficients at the two wavelengths, and calculate a value of oxygen saturation based on the ratio.

The processor may calculates the ratio of absorption coefficients by taking a ratio of the phase shift and a square root of the frequency for each the wavelength and each the frequency.

The processor may calculate the ratio of absorption coefficients by taking a ratio of the phase shifts detected at the two wavelengths. The phase shift of each the wavelength may be corrected for $\theta_0$.

The spectrophotometer may include a mechanism for positioning the input and detection ports at several selected relative distances.

The spectrophotometer may include a look up table comprising values of the scattering property for different tissue types. These values may be the effective scattering coefficients, $(1-g)\mu_s$.

The spectrophotometer may further include a magnitude detector constructed to measure an amplitude of the detected radiation. The processor may calculate the scattering property based on the measured amplitude. The processor may calculate the concentration by employing Eq. 5.

The absorptive pigment may be an endogenous pigment, such as oxy-hemoglobin or deoxy-hemoglobin. The absorptive pigment may be an exogenous contrast agent.

DESCRIPTION OF THE PREFERRED EMBODIMENTS

One preferred embodiment of the pathlength corrected oximeter utilizes three LEDs for generation of light at three selected wavelengths intensity modulated at a frequency of 50.1 MHz and coupled directly to the examined tissue. At each wavelength, the introduced light is altered by the tissue and is detected by a wide area photodiode placed against the skin. The introduced and detected radiations are compared to determine their relative phase shift that corresponds to an average pathlength of the migrating photons and, furthermore, the light attenuation is determined.

Figure 1:
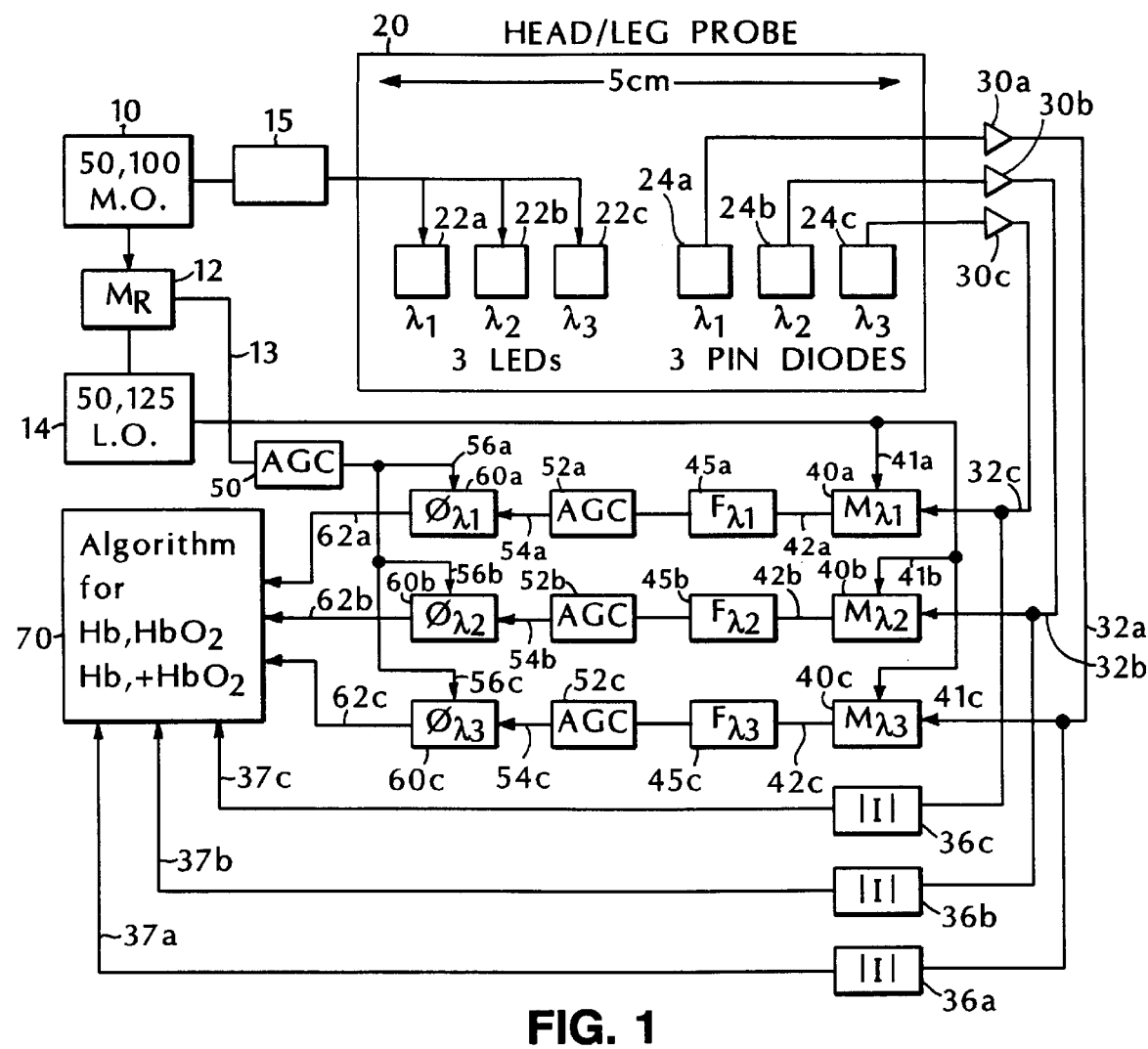
FIG. 1 is a block diagram of a pathlength corrected oximeter in accordance with the present invention.

Referring to FIG. 1, the oximeter includes a master oscillator 10 operating at 50.1 MHz connected to a power amplifier 15 of sufficient output power to drive LEDs 22a, 22b, and 22c (for example HLP 20RG or HLP 40RG made by Hitachi) that emit 760 nm, 840 nm, and 905 nm (or 950 nm) light, respectively. A second local oscillator 14 operating at 50.125 MHz and mixer 12 are used to generate a reference frequency 13 of 25 kHz. Each LED directly positioned on the skin has an appropriate heat sink to eliminate uncomfortable temperature increases that could also alter blood perfusion of the surrounding tissue. Three PIN diode detectors 24a, 24b, and 24c are placed at a distance of approximately 5 cm from the LEDs and have a detection area of about 1 cm$^2$. Photons migrating a few centimeters deep into the tissue are detected by the respective PIN diodes. The source-detector separation can be increased or decreased to capture deeper or shallower migrating photons. The signals from PIN diodes 24a, 24b, and 24c are amplified by preamplifiers 30a, 30b, and 30c, respectively.

The amplified signals (32a, 32b, 32c) are sent to magnitude detectors 36a, 36b, and 36c and to mixers 40a, 40b, and 40c, respectively. The magnitude detectors are used to determine intensity values of detected signals at each wavelength to be used in Eq. 1. Each mixer, connected to receive a 50.125 MHz reference signal (41a, 41b, 41c) from local oscillator 14, converts the detection signal to a 25 kHz frequency signal (42a, 42b, 42c). The mixers are high dynamic range frequency mixers, model SRA-1H, commercially available from Mini-Circuits (Brooklyn N.Y.). The detection signals (42a, 42b, and 42c) are filtered by filters 45a, 45b, 45c, respectively.

Phase detectors 60a, 60b, and 60c are used to determine phase shift between the input signal and the detected signal at each wavelength. Each phase detector receives the 25 kHz detection signal (54a, 54b, 54c) and the 25 kHz reference signal (56a, 56b, 56c), both of which are automatically leveled by automatic gain controls 50 and 52 to cover the dynamic range of signal changes. Phase detectors 60a, 60b, and 60c generate phase shift signals (62a, 62b, 62c) corresponding to the migration delay of photons at each wavelength. Each phase shift signal is proportional to the migration pathlength used in calculation algorithms performed by processor 70.

Figure 2:
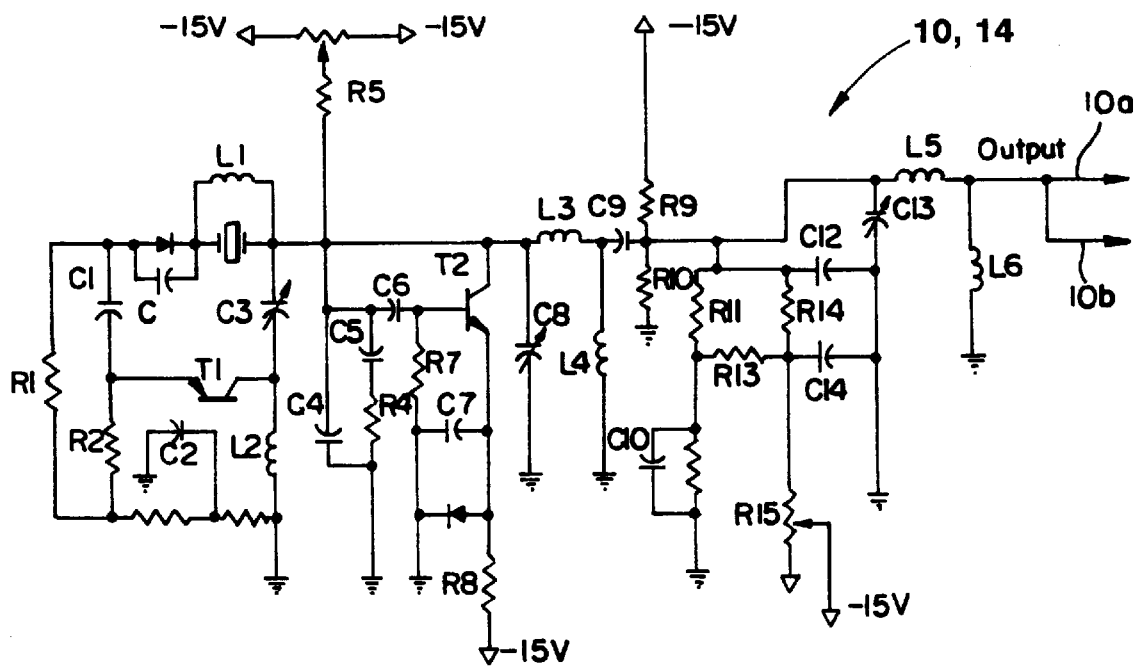
FIG. 2 is a schematic circuit diagram of a 50.1 MHz (50.125 MHz) oscillator used in the oximeter of FIG. 1.

FIG. 2 shows a schematic circuit diagram of a precision oscillator used as the 50.1 MHz master oscillator 10 and 50.125 MHz local oscillator 14. The oscillator crystals are neutralized for operation in the fundamental resonance mode; this achieves long-term stability. Both oscillators are thermally coupled so that their frequency difference is maintained constant at 25 kHz if a frequency drift occurs.

Figure 3:
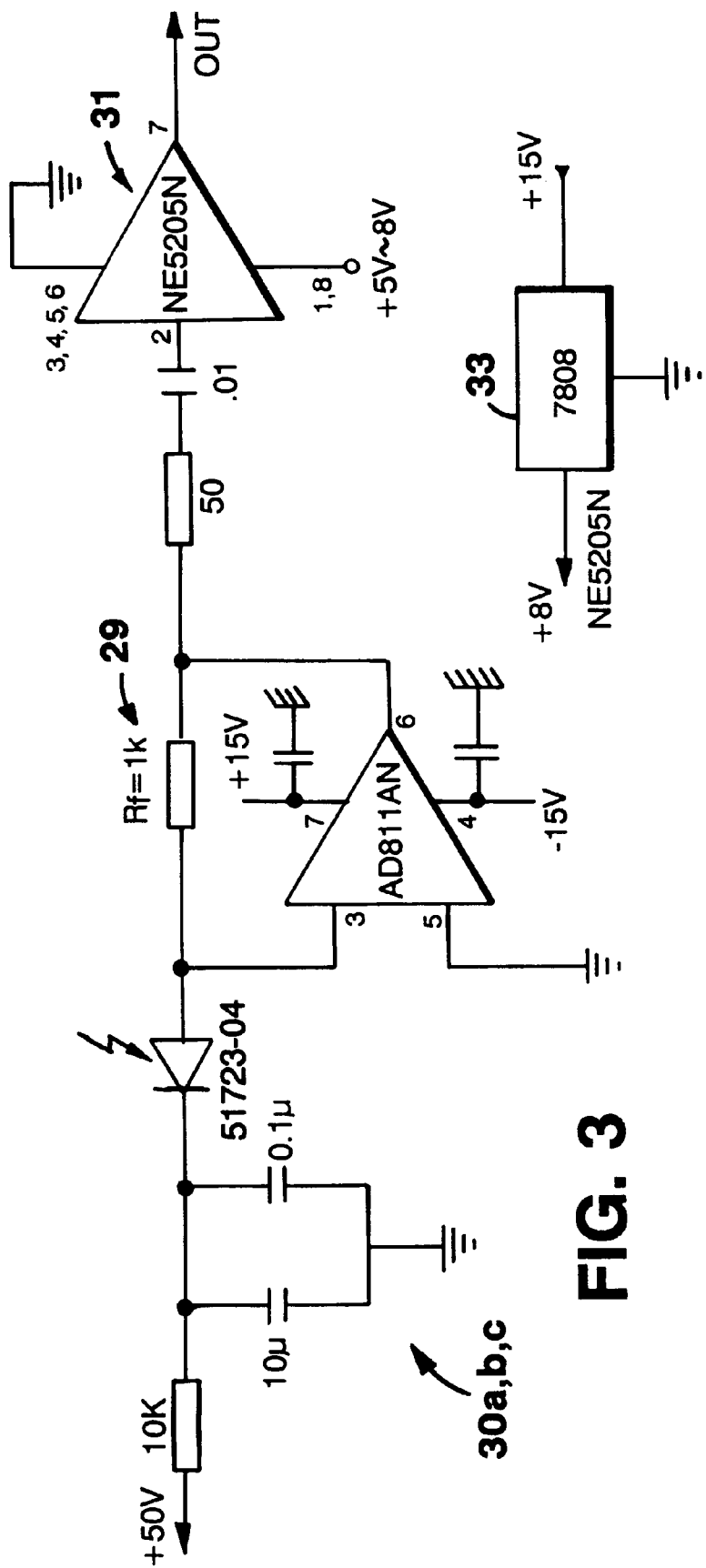
FIG. 3 is a schematic circuit diagram of a PIN diode and a preamplifier used in the oximeter of FIG. 1.
Figure 4:
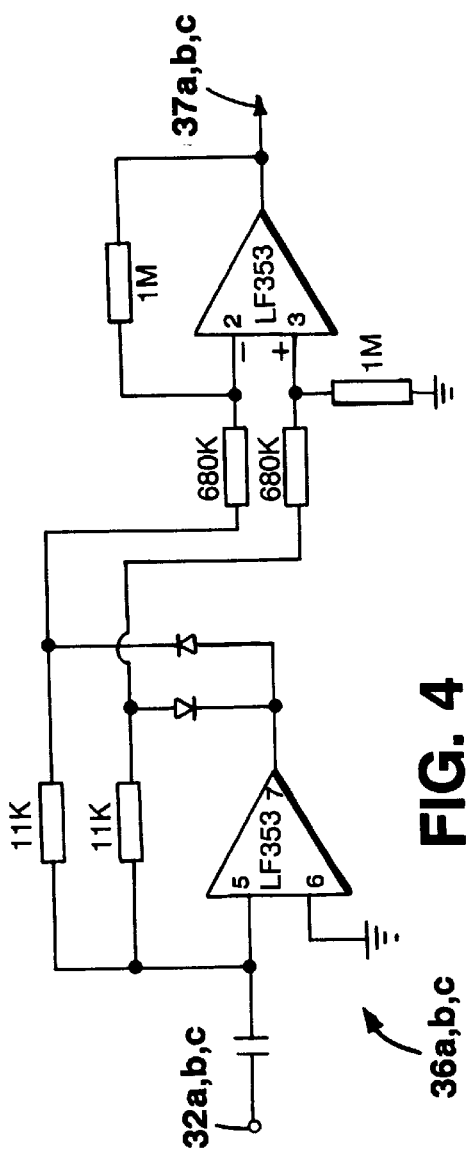
FIG. 4 is a schematic circuit diagram of a magnitude detector used in the oximeter of FIG. 1.

PIN diodes 24a, 24b, and 24c are directly connected to their respective preamplifiers 30a, 30b, and 30c, as shown in FIG. 3. The oximeter uses PIN silicon photodiodes S1723-04 with 10 mm×10 mm sensitive area and spectral response in the range of 320 nm to 1060 nm. The detection signal is amplified by stages 29 and 31, each providing about 20 dB amplification. The NE5205N operational amplifier is powered at +8V to operate in a high gain regime. The 8V signal is supplied by a voltage regulator 33. The amplified detection signals (32a, 32b, and 32c) are sent to magnitude detectors 36a, 36b, and 36c, shown in FIG. 4. The magnitude values (37a, 37b, and 37c) are sent to processor 70 that calculates the light attenuation ratio or logarithm thereof as shown Eq. 1.

Figure 5:
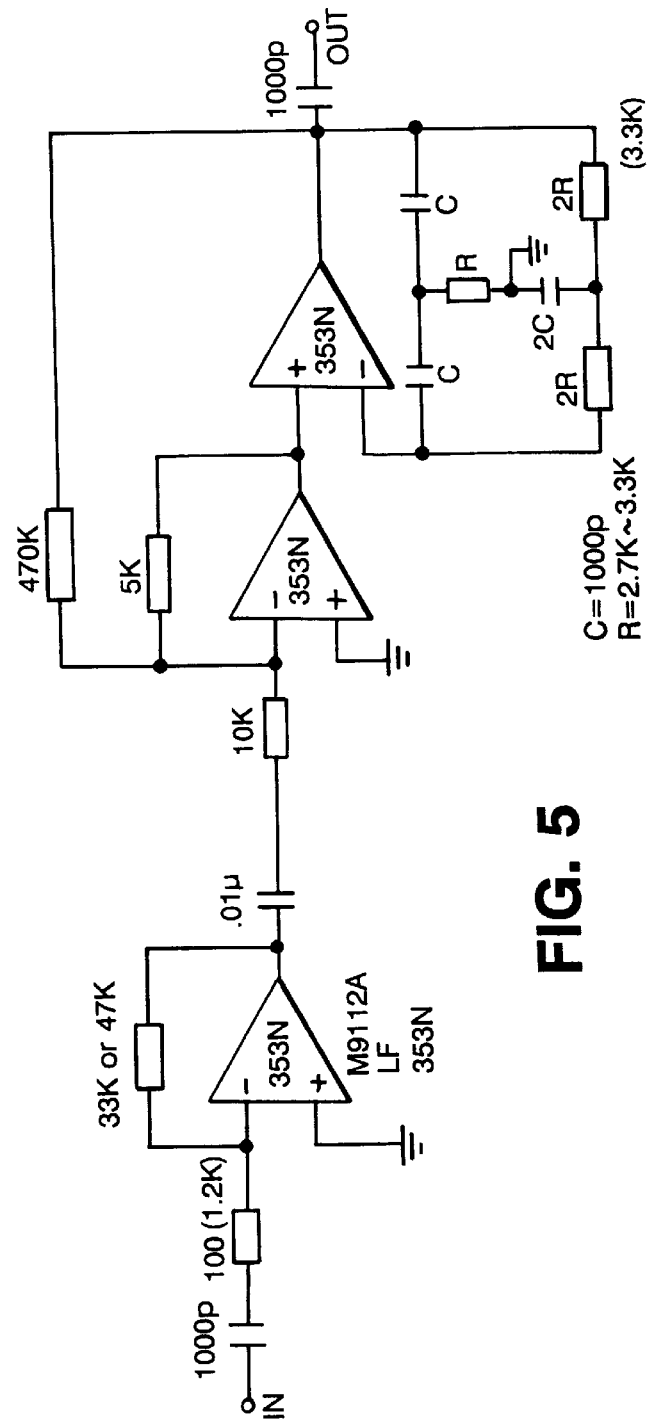
FIG. 5 is a schematic circuit diagram of a 25 kHz filter used in the oximeter of FIG. 1.

Also referring to FIG. 5, the AGC circuit uses MC 1350 integrated circuit for amplification that maintains the input signal of phase detector 60 at substantially constant levels. The amount of gain is selected to be equal for AGCs, 50 and 52. The signal amplitude is controlled by a feedback network 53. The AGCs provide a substantially constant amplitude of the detected and reference signals to eliminate variations in the detected phase shift due to cross talk between amplitude and phase changes in the phase detector.

Figure 6:
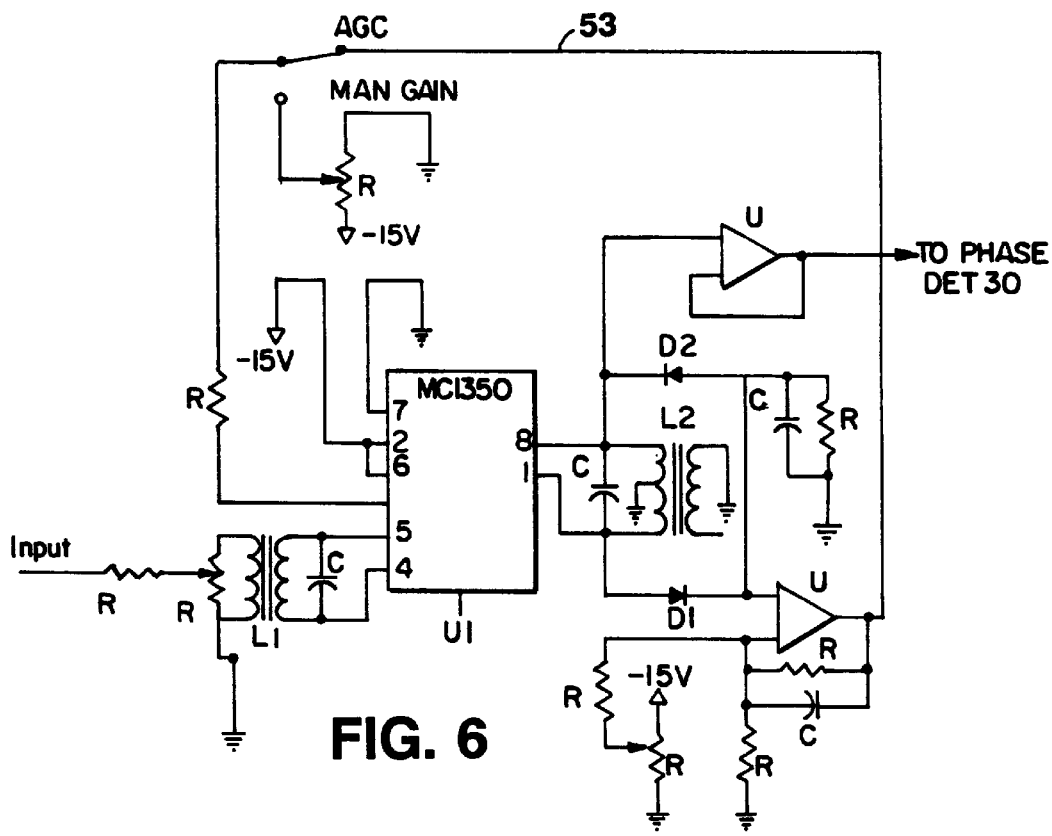
FIG. 6 is a schematic diagram of an AGC circuit of the oximeter of FIG. 1.
Figure 7:
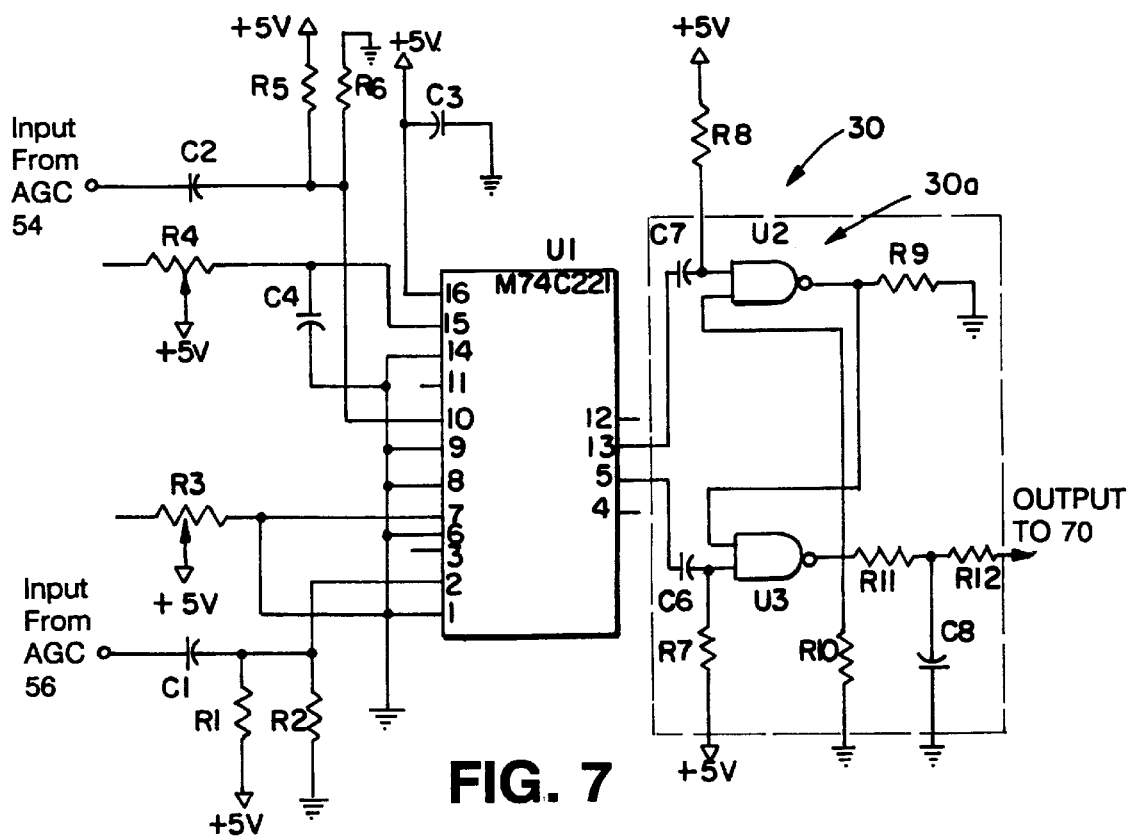
FIG. 7 is a schematic circuit diagram of a phase detector of the oximeter of FIG. 1.

Referring to FIG. 6, each phase detector includes a Schmitt trigger that converts the substantially sinusoidal detection signal (54a, 54b, 54c) and reference signal (56a, 56b, 56c) to square waves. The square waves are input to a detector that has complementary MOS silicon-gate transistors. The phase shift signal is sent to processor 70.

The oximeter is calibrated by measuring the phase shift for a selected distance in a known medium, i.e., using a standard delay unit, and by switching the length of a connector wire to change the electrical delay between master oscillator 10 and local oscillator 14.

Figure 8A:
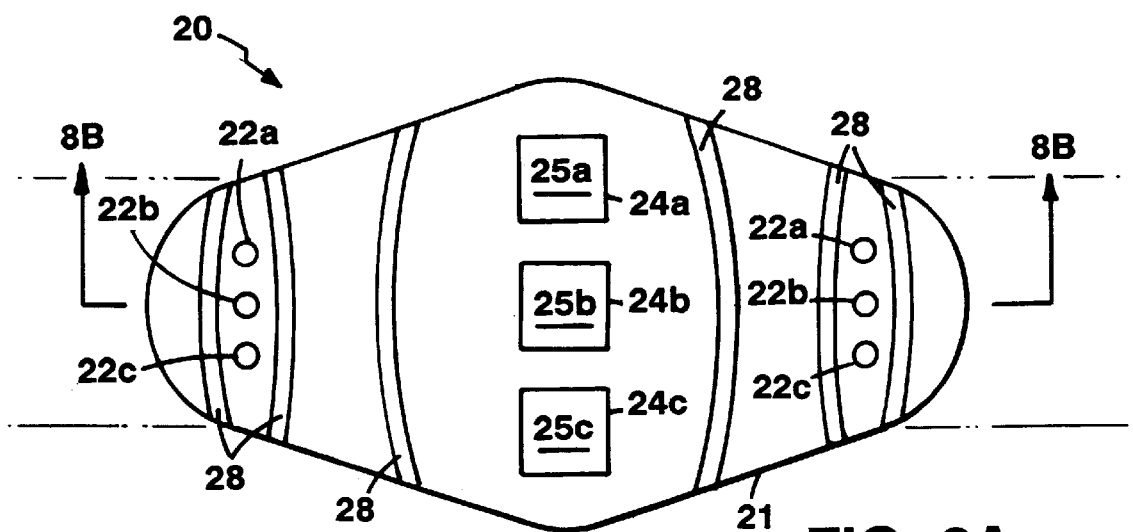
FIG. 8A is a plan view of a source-detector probe of the oximeter.
Figure 8B:
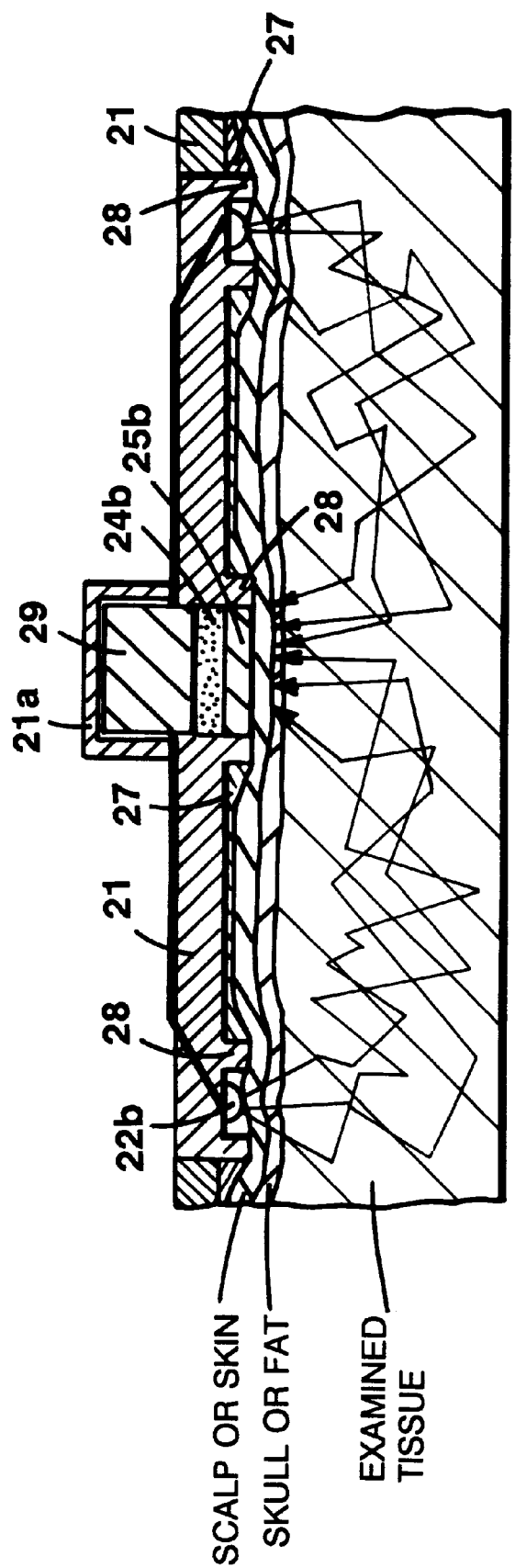
FIG. 8B is a transverse cross-sectional view taken on lines 8B of FIG. 8A further showing the photon migration.

Referring to FIGS. 8A and 8B source-detector probe 20 includes several LEDs (22a, 22b, 22c) of selected wavelengths and PIN photodiodes (24a, 24b, 24c) mounted in a body-conformable support structure 21. Structure 21 also includes a photon escape barrier 27 made of a material with selected scattering and absorption properties (for example, styrofoam) designed to return escaping photons back to the examined tissue. The support structure further includes a second conformable barrier 28, located between the LEDs and the diode detectors, designed to absorb photons directly propagating from the source to the detector and thus prevent detection of photons that migrate subcutaneously. Support structure 21 also includes electronic circuitry 29 encapsulated by an electronic shield 21a.

Each PIN diode is provided with an evaporated single wavelength film filter (25a, 25b, 25c). The filters eliminate the cross talk of different wavelength signals and allow continuous operation of the three light sources, i.e., no time sharing is needed.

The use of photodiode detectors has substantial advantages when compared with the photomultiplier tube used in standard phase modulation systems. The photodiodes are placed directly on the skin, i.e., no optical fibers are needed. Furthermore, there is no need to use a high voltage power supply that is necessary for the photomultiplier tube. The photodiodes are much smaller and are easy to place close to the skin. Advantages of the photomultiplier tube are a huge multiplication gain and a possibility of direct mixing at the photomultiplier; this cannot be achieved directly by a photodiode. This invention envisions the use of several different photodiodes such as PIN diode, avalanche diode, and other.

The processor uses algorithms that are based on equations described by E. M. Sevick et al. in "Quantitation of Time- and Frequency-Resolved Optical Spectra for the Determination of Tissue Oxygenation," published in Analytical Biochemistry 195, 330, Apr. 15, 1991, which is incorporated by reference as if fully set forth herein. The photon migration in biological tissue is a diffusional process in which the photon fluence rate, $\phi$ (r,t), is distributed from the source.

The fluence rate is equal to $N_\alpha c$, or the product of the number of the photon at position r and time, t, and the speed of photons through the medium. The fluence rate, or the effective "concentration" of photons at position r and time t, in the tissue or turbid media may be obtained from the solution of the general diffusion equation $$\frac{1}{c}\frac{\partial}{\partial t}\phi(r, t) - D\nabla^2 \phi(r, t) + \mu_a \phi(r, t) = S(r, t) \qquad (2)$$

where D is the diffusion coefficient and S a source term. For photon migration, the diffusion coefficient is equal to $$D = \frac{1}{3\mu_a + (1-g)\mu_s} \qquad (3)$$

where $\mu_s$ is the scattering coefficient (cm$^{-1}$) and g is the mean cosine of scattering angle. The term $(1-g)\mu_s$ is referred to as the effective scattering coefficient and is equal to the reciprocal of the isotropic, mean scattering length, l* (i.e., when the direction of scatter is completely random). The absorption coefficient $\mu_a$ is based upon the Napierian extinction coefficient.

The source at $\rho=0$ consists of light whose intensity is sinusoidally modulated at a frequency f. The light intensity detected at a distance $\rho$ away from the source is both amplitude demodulated and phase shifted with respect to the incident source intensity. The measured phase shift, $\theta$, and the modulation, M, of the detected light with respect to that of the incident light characterize the tissue wherein the detected photons migrated over a distribution of pathlengths. The phase shift describes the pathlength distribution in the frequency domain. It can be directly related to the mean of the distribution of pathlengths traveled by photons before detection. The modulation of the detected intensity also varies with changes in the absorbance and pathlength distribution. Pathlengths can be used to detect changes in absorption in strongly scattering media. Modulation may also be used to detect changes in absorption in the tissue. In phase modulation (frequency modulation), the source term represents a sinusoidally modulated photon flux at point $\rho=0; S(\rho=0, t)=A+M\cdot\sin(2\pi f\cdot t)$. Expressions of the phase shift and modulation of the detected intensity may also be directly found from Eq. 2.

The analytical solution for $\theta$ and M can be obtained from the sine and cosine Fourier transforms of Eq. 2:

$$\theta(\rho, f) = -\psi\sin\frac{\Theta}{2} - \tan^{-1}\frac{-\psi\sin\frac{\Theta}{2}}{1+\psi\cos\frac{\Theta}{2}} \qquad (4)$$

$$M(\rho, f) = \frac{\left(1+\psi^2+2\psi\cos\frac{\Theta}{2}\right)^{1/2}}{(1+\psi_\infty)}\exp\left(\psi_\infty - \psi\cos\frac{\Theta}{2}\right) \qquad (5)$$

where: $\qquad (6)$ $$\psi = \sqrt{3(1-g)\mu_s \rho^2\{(\mu_a c)^2 + (2\pi f)^2\}^{1/2} C^{-1}}, \psi_\infty = \psi(f=0)$$

$$\Theta = \tan^{-1}\left\{\frac{2\pi f}{\mu_a c}\right\} \qquad (7)$$

At each wavelength, for low modulation frequencies, i.e., $2\pi f \ll \mu_a \cdot c$, the phase shift ($\theta^\lambda$) (62a, 62b, 62c) is used to calculate the pathlength as follows:

$$\theta^\lambda = \tan^{-1} \pi f \langle t^\lambda \rangle = \tan^{-1} \frac{2\pi f \langle L^\lambda \rangle}{c} \approx \frac{2\pi f \langle L^\lambda \rangle}{c} \quad (8)$$

wherein f is modulation frequency of the introduced light which is in the range of 10 MHz to 100 MHz; $t^\lambda$ is the photon migration delay time; c is the speed of photons in the scattering medium; and $L^\lambda$ is the migration pathlength. The modulation frequency of 50 MHz was selected due to the frequency limitation of the LEDs and photodiodes. However, 10 for faster LEDs and photodiodes it may be desirable to use higher modulation frequencies that increase the phase shift resolution.

At high modulation frequencies, i.e., $2\pi f \gg \mu_a \cdot c$, the phase shift is no longer proportional to the mean time of flight $\langle t \rangle$.

$$\theta^\lambda = a\rho\sqrt{(1-g)\mu_s f}\left\{1 - \frac{\mu_a^\lambda c}{4\pi f}\right\} \quad (9)$$

$$\theta_0^\lambda = a\rho\sqrt{(1-g)\mu_s f}\left\{1 - \frac{\alpha^\lambda c}{4\pi f}\right\} \quad (10)$$

wherein $\rho$ is the source-detector separation; $a = (6\pi/c)^{1/2}$. $\sin\pi/4$; $(1-g)\mu_s$ is the effective scattering coefficient, $\mu_a^\lambda$ is the absorption coefficient at wavelength $\lambda$, $\alpha^\lambda$ is the background absorbance at wavelength $\lambda$, and $\theta_0^\lambda$ thus represents background scattering and absorption. At two wavelengths, the ratio of absorption coefficients is determined as follows:

$$\frac{\mu_a^{\lambda_1}}{\mu_a^{\lambda_2}} = \frac{\theta^{\lambda_1} - \theta_0^{\lambda_1}}{\theta^{\lambda_2} - \theta_0^{\lambda_2}} \quad (11)$$

The wavelengths are in the visible and infra-red range and are selected to have absorbance sensitive (or insensitive) to various tissue components such as water, cytochrome iron and copper, oxy- and deoxygenated forms of hemoglobin, myoglobin, melanin, glucose and other.

For oxygenated and deoxygenated hemoglobin, the absorption coefficient written in terms of Beer Lambert relationship is as follows:

$$\mu_a^{\lambda_1} = \epsilon_{Hb}^{\lambda_1}[Hb] + \epsilon_{HbO}^{\lambda_1}[HbO_2] + \alpha^{\lambda_1} \quad (12)$$

wherein $\epsilon_{Hb}^{\lambda_1}$ and $\epsilon_{HbO}^{\lambda_1}$ are extinction coefficients for hemoglobin and deoxyhemoglobin that can be stored in a look up table; [Hb], [HbO$_2$] are the tissue concentration of hemoglobin and oxyhemoglobin, respectively; $\alpha^{\lambda_1}$ is background absorbance at wavelength $\lambda_1$.

Tissue hemoglobin saturation can also be determined from dual-wavelength, dual-frequency measurements of the phase shift. For high modulation frequencies, $(2\pi f_1 \gg \mu_a^{\lambda_1} c$ and $2\pi f_2 \gg \mu_a^{\lambda_2} c)$ the differences in the measured phase shift at one wavelength and two frequencies can be expressed as $$\frac{\theta_{f_1}^{\lambda_1}}{\sqrt{f_1}} - \frac{\theta_{f_2}^{\lambda_1}}{\sqrt{f_2}} = \sqrt{\frac{6\pi(1-g)\mu_s\rho^2}{c}} \sin\frac{\pi}{4} \frac{\mu_a^{\lambda_1}}{4\pi}\left\{\frac{1}{f_2} - \frac{1}{f_1}\right\} \quad (13)$$

The ratio of this difference measured at two wavelengths can thus be written $$\frac{(\theta_{f_1}^{\lambda_1}/\sqrt{f_1}) - (\theta_{f_2}^{\lambda_1}/\sqrt{f_2})}{(\theta_{f_1}^{\lambda_2}/\sqrt{f_1}) - (\theta_{f_2}^{\lambda_2}/\sqrt{f_2})} = \frac{\mu_a^{\lambda_1}}{\mu_a^{\lambda_2}}. \quad (14)$$

Since the scattering coefficient is wavelength-insensitive over the near-infrared range employed, this dual-frequency, dual-wavelength phase modulated spectroscopy can be used to obtain the ratio of absorption coefficients.

Furthermore, as predicted from the diffusion approximation, the magnitude of the phase shift increases with the source-detector separation, $\rho$. Thus, in homogeneous tissues, the phase shifts measured for several $\rho$ can be used to calculate the absorption and scattering coefficients. These coefficients can be used either by employing Eq. 4 or the equations for the high and low approximations. Similarly, the magnitude of the detected radiation can be measured for different source-detector separations, and the absorption and scattering coefficients can be calculated by using Eq. 5.

The hemoglobin saturation is conventionally defined as follows:

$$Y = \frac{[HbO_2]}{[Hb] + [HbO_2]} \quad (15)$$

For a three wavelength measurement, the hemoglobin saturation can be calculated using Eqs. (12) and (15) as follows:

$$Y = \frac{a(\epsilon_{Hb}^{\lambda_3} - \epsilon_{Hb}^{\lambda_2}) - (\epsilon_{Hb}^{\lambda_1} - \epsilon_{Hb}^{\lambda_2})}{[(\epsilon_{HbO_2}^{\lambda_1} - \epsilon_{HbO_2}^{\lambda_2}) - (\epsilon_{Hb}^{\lambda_1} - \epsilon_{Hb}^{\lambda_2})] - a[(\epsilon_{HbO_2}^{\lambda_3} - \epsilon_{HbO_2}^{\lambda_2}) - (\epsilon_{Hb}^{\lambda_3} - \epsilon_{Hb}^{\lambda_2})]} \quad (16)$$

where $$a = \frac{\mu_a^{\lambda_1} - \mu_a^{\lambda_2}}{\mu_a^{\lambda_3} - \mu_a^{\lambda_2}} \quad (17)$$

Thus, processor 70 determines Y from the above equations for each wavelength $\lambda_1$, $\lambda_2$, $\lambda_3$.

In another embodiment, the spectrophotometer's electronics includes a low frequency module suitably and a high frequency module switchably coupled to the same source-detector probe 20. The low frequency module and the arrangement of the source-detector probe are substantially similar to the hemoglobinometer described in a co-pending U.S. patent application Ser. No. 701,127 filed May 16, 1991 which is incorporated by reference as if fully set forth herein. The low frequency module corresponds to a standard oximeter with modulation frequencies in the range of a few hertz to $10^4$ hertz and is adapted to provide intensity attenuation data at two or three wavelengths. Then, the LEDs are switched to the high frequency phase modulation unit, similar to the unit of FIG. 1, which determines the average pathlength at each wavelength. The attenuation and pathlength data are sent to processor 70 for determination of a physiological property of the examined tissue.

Figure 9:
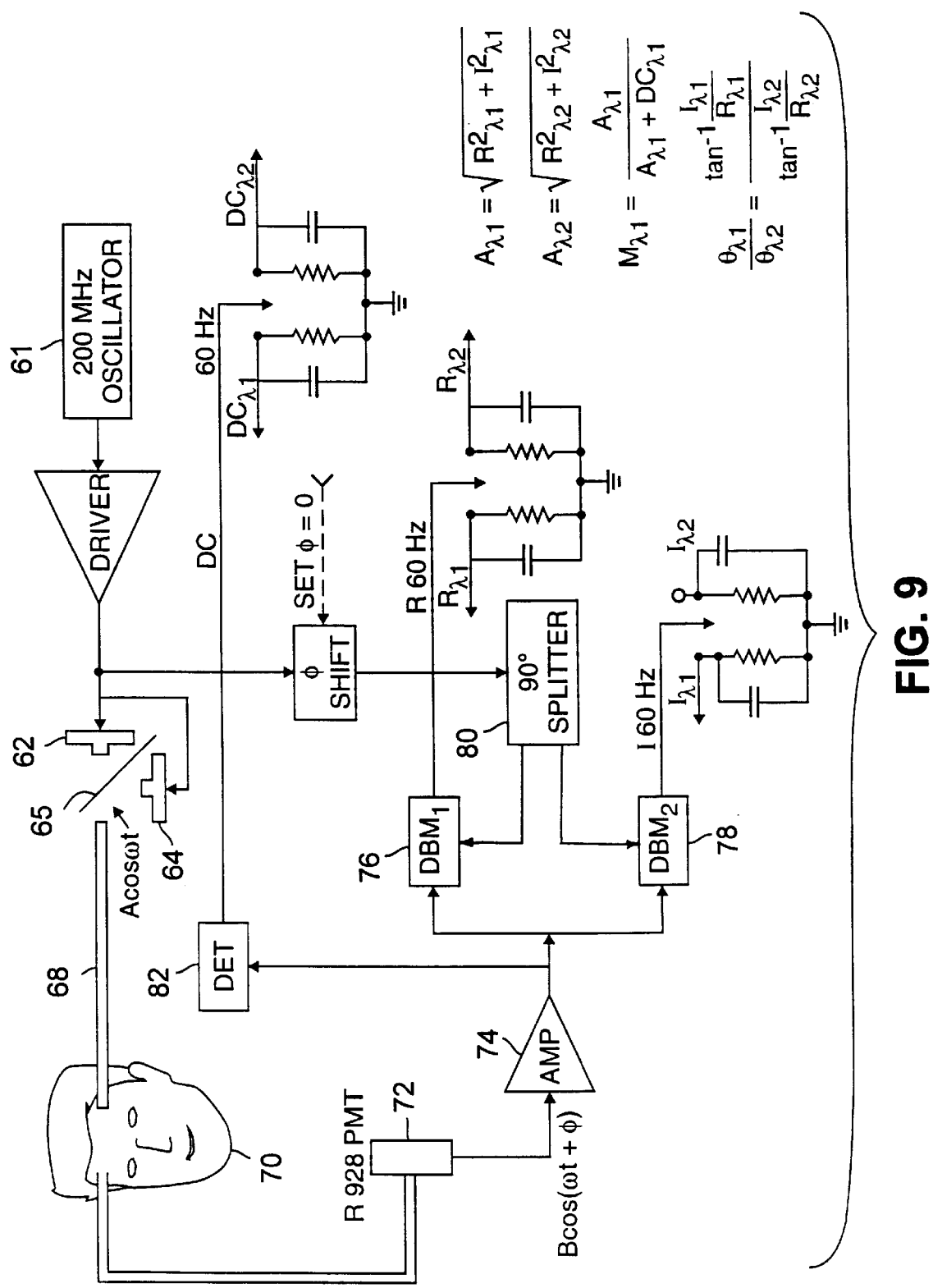
FIG. 9 is a block diagram of another embodiment of a phase modulation spectrophotometer.

In another embodiment, the pathlength corrected oximeter utilizes the same LED sources (22a, 22b, 22c) sinusoidally modulated at a selected frequency comparable to the average migration time of photons scattered in the examined tissue on paths from the optical input port of the LED's to the optical detection part of the photodiode detectors (24a, 24b, 24c), but the electronic circuitry is different. Referring to FIG. 9, this embodiment utilizes a 200 MHz precision oscillator 61, which drives two laser diodes 62 and 64, again at 760 and 816 nm. The outputs of the laser diodes are time shared into filter optic coupling 68 and the head 70. Detector 72 provides output to an amplifier 74 and to two wide band double balance mixers (DBM) 76 and 78 which are coupled through a 90° phase splitter 80 so that real (R) and imaginary (I) portions of the signal are obtained. The double balance mixers 76 and 78 preferably operate at the modulation frequency. The phase ($\theta^\lambda$) is the angle whose tangent is the imaginary over the real part.

$$\theta^\lambda = \tan^{-1} \frac{I^\lambda}{R^\lambda} \quad (18)$$

The amplitude is the square root of the sum of the squares of these values, providing the phase shift has been taken out as the residual phase shift θ 0 set to zero.

$$A^\lambda = \sqrt{(R^\lambda)^2 + (I^\lambda)^2} \quad (19)$$

This embodiment uses summing and dividing circuits to calculate the modulation index, which is the quotient of the amplitude over the amplitude plus the DC component obtained from a narrow band detector 82.

$$M^\lambda = \frac{A^\lambda}{A^\lambda + DC^\lambda} \quad (20)$$

The phase processor receives the phase shifts for the phase and amplitude values for two or three wavelengths and calculates the ratio of the phase shifts. For each wavelength, the phase shift and the DC amplitude are used to determine a selected tissue property, e.g., hemoglobin oxygenation.

Figure 10A:
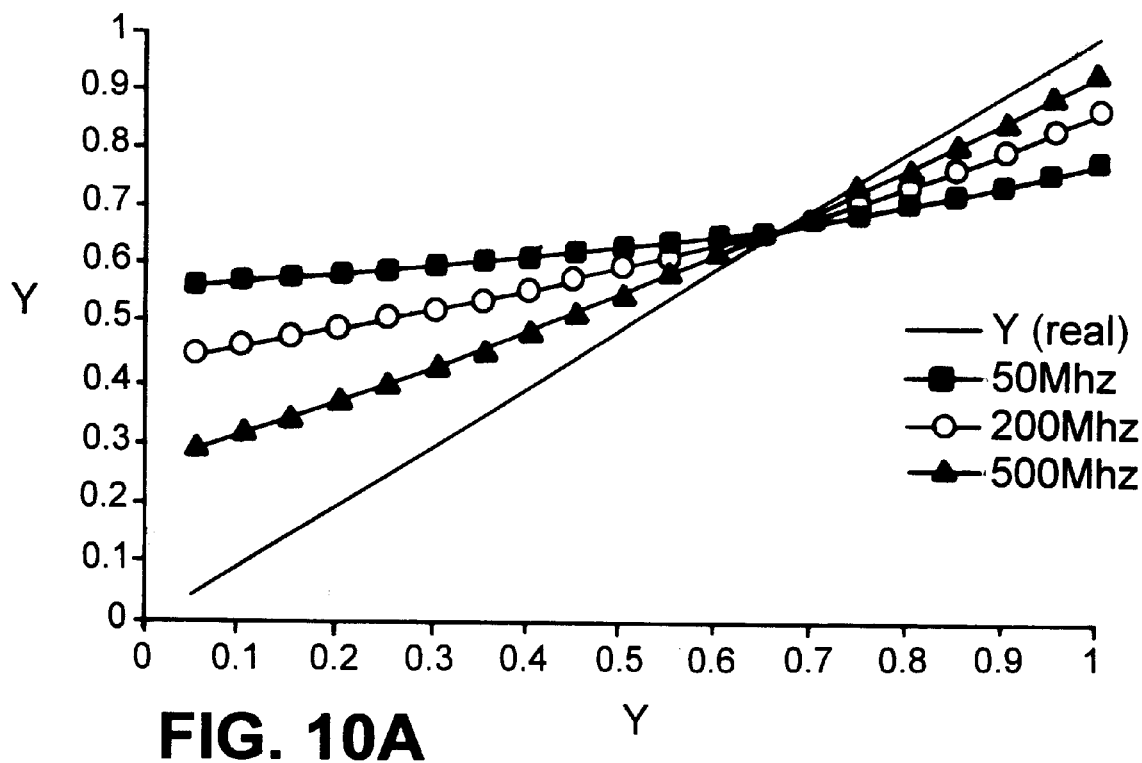
FIGS. 10A and 10B display simulation results for oxygen saturation values and their noise dependence, respectively, calculated by using a high frequency approximation.
Figure 10B:
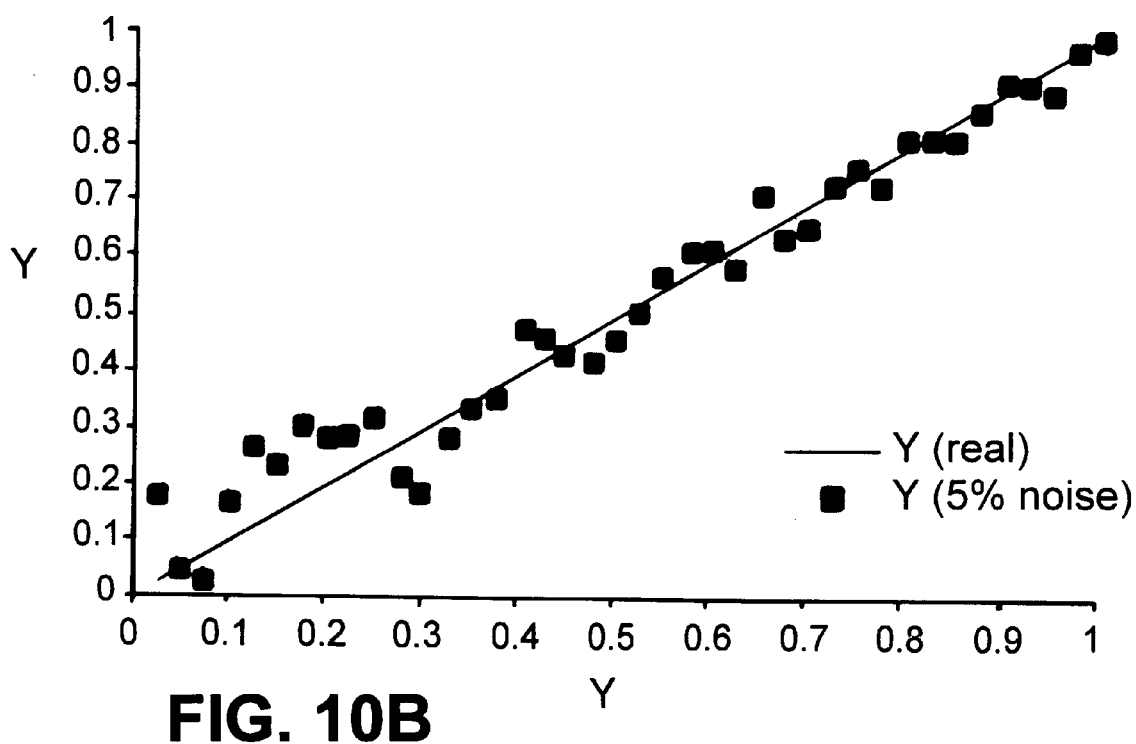

To study the influence of variation in the scattering coefficient on the quantitation of the absorption measurements, several simulations were performed. The simulations assumed the phase shift measurements at two wavelengths and several frequencies (10 MHz, 50 MHz, 200 MHz and 500 MHz). Hemoglobin saturation levels (Y) were varied in the range of 5%≦Y≦100%, and the absorption coefficients were varied in the range of $0.5 \leq \mu_a \leq 1.5$ cm$^{-1}$, while the scattering coefficient $\mu_s'=5$ cm$^{-1}$ was kept constant; these values correspond to typical values for human tissue. FIGS. 10A and 10B show simulation results obtained by using the high frequency approximation ($2\pi f \gg \mu_a c$) for modulation frequencies f=50, 200 and 500 MHz, assuming $\theta_0^{\lambda 1}=\theta_0^{\lambda 2}=\theta_0$, and $\mu_a c \approx 2 \cdot 10^9 \cdot \theta_0$. As shown in FIG. 10A, the calculated saturation error decreases with frequency, but still introduces a significant error even for the 500 MHz at low saturation values. FIG. 10B shows the influence of added 5% noise for f=500 MHz. Low saturation values exhibit greater sensitivity to the introduced noise than high saturation values.

The high sensitivity at low saturation values is expected for the high frequency approximation (Eq. 11). While the absorption coefficient for an isobestic wavelength does not change with saturation, lower saturation values yield lower values of the absorption coefficient for a contrabestic oxyhemoglobin wavelength; this yields lower values of $\theta^{\lambda 2}-\theta_0$ in the denominator of Eq. 11. Thus, the $\mu_a$ ratio, at the two wavelengths, is more sensitive to noise at low saturation values.

Figure 11A:
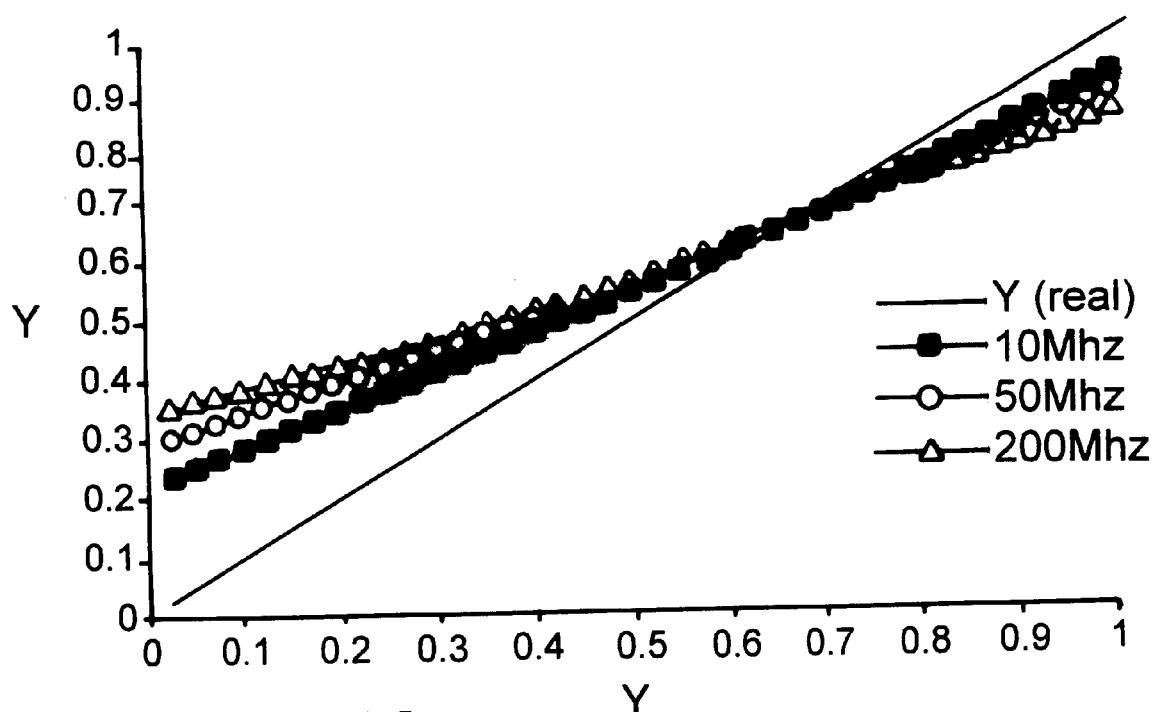
FIGS. 11A and 11B display simulation results for oxygen saturation values and their noise dependence, respectively, calculated by using a low frequency approximation.
Figure 11B:
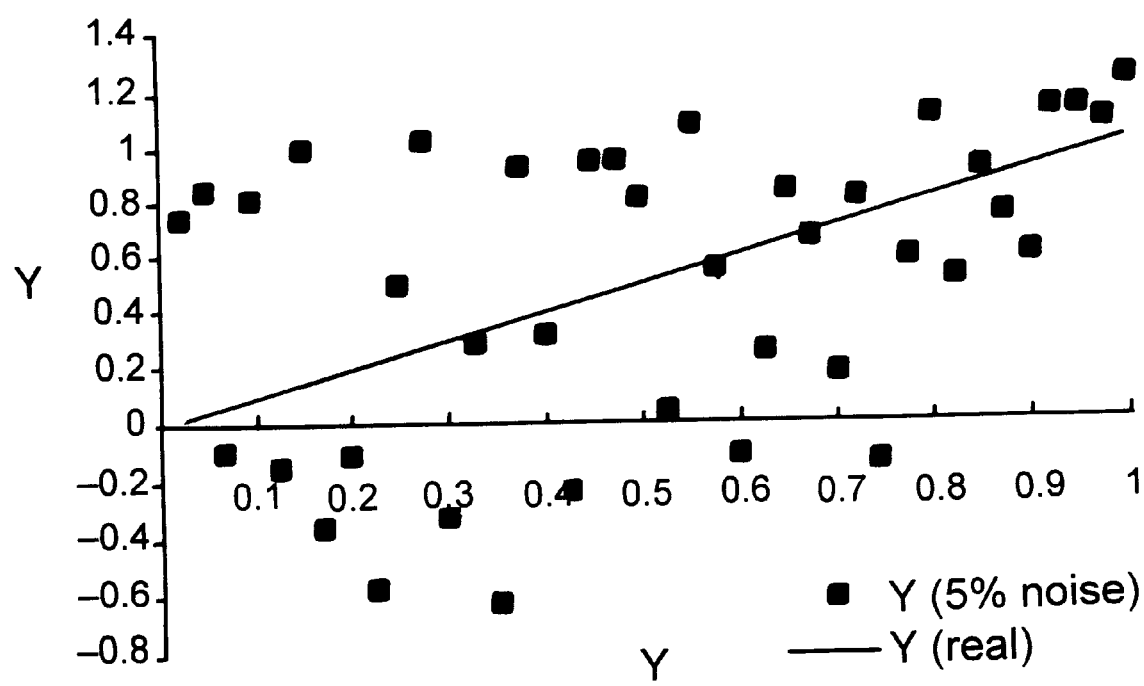

FIGS. 11A and 11B show simulation results obtained using the low frequency approximation ($2\pi f \gg \mu_a c$) for modulation frequencies f=10, 50 and 200 MHz, assuming $\theta_0^{\lambda 1}=\theta_0^{\lambda 2}=\theta_0$, and $\mu_a c \approx 2 \cdot 10^9 \cdot \theta_0$. As shown in FIG. 11A, the low frequency approximation introduces lower error for the "intermediate" frequency of 200 MHz than the high frequency approximation shown in FIG. 10A. However, the low frequency approximation is much more sensitive to noise as shown in FIG. 11B. The relatively high sensitivity is again expected because the ratio of the absorption coefficients at the two wavelengths is obtained from the square the phase shift ratio, i.e., $\mu_a^{\lambda 2}/\mu_a^{\lambda 1}=(\theta^{\lambda 1}/\theta^{\lambda 2})^2$.

Thus, when using the high and low frequency approximation, the calculated data may need to be corrected. The correction can be made by using look-up tables or other methods, such as dual frequency phase modulation measurement (Eq. 14) or phase modulation measurements with dual source-detector separation, to obtain more accurate information about the background phase shift.

Figure 12:
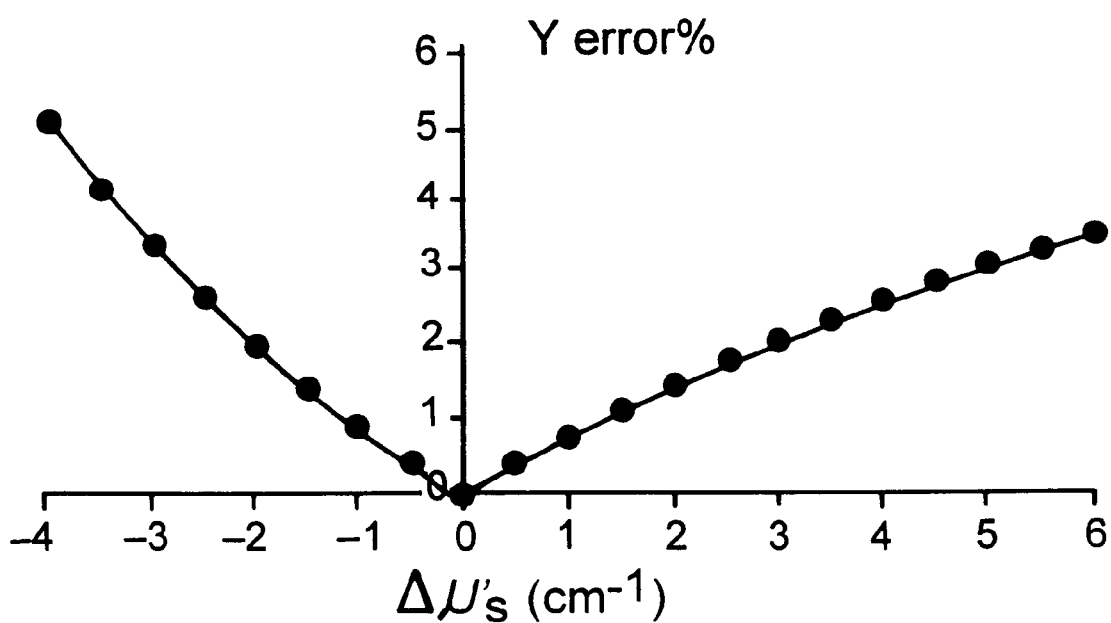
FIG. 12 displays simulation results for oxygen saturation values as a function of a varying scattering coefficient.

FIG. 12 shows simulation results for the oxygen is saturation obtained using Eq. 4 to calculate the ratio of absorption coefficients at the two wavelengths. This simulation assumed a correct value of the effective scattering coefficient ($\mu_s'=7$ cm$^{-1}$) and varied the "selected" tissue saturation (and thus the tissue absorption). For each "selected" saturation, the simulation calculated the absorption coefficient solving Eq. 4, while numerically varying $\mu_s'$ from 3 cm$^{-1}$ to 13 cm$^{-1}$ using the Newton-Raphson method. For each $\mu_s'$, the error in the calculated saturation Y was calculated by subtracting the "selected" saturation from the "back-calculated" saturation. As shown in FIG. 12, for example, for a error of 3 cm$^{-1}$ in $\mu_s$, the mean error in Y is about 2.5%, while the standard deviation does not exceed 1.59%. Thus, by employing Eq. 4, the phase modulation system can use an approximate value of the effective scattering coefficient to measure the oxygen saturation. The oxygen saturation is quite insensitive to the selection of the effective scattering coefficient as the introduced error is reduced by taking the ratio of the absorption coefficients.

The phase modulation system is calibrated initially and may be recalibrated after several measurements to obtain a correct phase reading and an average drift. Another type of a phase modulation system is PMD-3000 (available from NIM Incorporated, Philadelphia, Pa.), which is also described in U.S. Pat. No. 5,122,974. This phase modulation system uses two laser diodes at 754 nm and 780 nm, each having an average signal power 5 mW. The two wavelengths are time shared using a mechanical shutter before the light is introduced in the tissue and then detected by a Hamamatsu R928 PMT detector. The system uses two frequencies of 200.000 MHz and 200.025 MHz, and the detected signal is demodulated by heterodyning the second dynode of the PMT detector. The detected amplitude is used in a feed-back loop as an automatic gain control.

The phase detector of the system provides a voltage output that is converted then to the phase as specified by the manufacturer. There are several techniques to determine the voltage-to-phase conversion curve, which ideally should be linear and the precision should be better that 0.1°. The conversion curve can be verified by changing the pathlength of the electrical or optical signal by changing the physical length of an electrical line. Here, one has to watch for a line mismatch that can potentially create measurement problems. Alternatively, the conversion curve can be verified by changing the source detector separation on an optical bench and measuring the corresponding voltage difference at the output of the phase detector. One has to prevent the phase amplitude cross-talk and operate the system at a proper signal-to-noise level.

Alternatively, one can simulate a real experiment by using a tank containing an Intralipid™ solution of known absorption and scattering properties. (See Sevick et al., Analytical Biochemistry Vol. 195, p. 341.) The source-detector geometry resembles the actual tissue measurement geometry. The measured absorption coefficient can thus be compared to the known absorption coefficient. The voltage-to-phase curve is calibrated by taking multiple points at different blood concentrations.

The phase modulation system also has a reference phase ($\theta_{instr}$) that of course affects $\theta_0$. The instrumental reference phase can be determined empirically or can be measured by butt-coupling the source and detector fibers. In this arrangement, the detected optical signal should be attenuated with a neutral density or NTR filter so the detector works in the same signal power range as for the in vivo tissue measurements.

The instrumental reference phase can also be measured using a dual channel phase modulation system that provides both a phase output and an amplitude output. In this measurement, the above model should have similar scattering and no absorption, or known scattering and absorbing properties. The dual channel phase modulation system can resolve both $\mu_s'$ and $\mu_a$, which in turn are used to calculate the instrumental reference phase. Furthermore, the instrumental reference phase can also be determined by measuring the phase shift at different source-detector separations.

The phase modulation system can use the amplitude in a feedback arrangement to control the laser intensity. (This type of feedback is similar to the automatic gain control (AGC) technique described above.) The intensity is adjusted in discrete steps so that no change in the laser intensity occurs during the measurement. This feedback system can measure tissue at a wide range of source-detector separations or background absorptions; there is no need to select an optical attenuator or adjust the gain (high voltage) of the detector. Furthermore, the detector can be operated in the optimum high voltage for all measurements.

In an experimental study, six newborn piglets, age one to five days, were used (average weight—2.0 kg). After anesthesia and surgery, they were randomized either to preexisting mixed acidosis with a pH less than 7.00 and a $pCO_2$ larger than 8.0 kPa, or a normal pH and $pCO_2$. The acidosis was induced by infusing lactic acid in a vein, and $CO_2$ was added to the inspired air. Once the piglets were stabilized, the fraction of oxygen in the inspired air (the $FiO_2$) was reduced from 21% to 6% for 30–40 minutes and then the piglets were resuscitated. Mean arterial blood pressure was kept above 40 mmHg at all times using an intravenous adrenaline infusion.

Figure 13A:
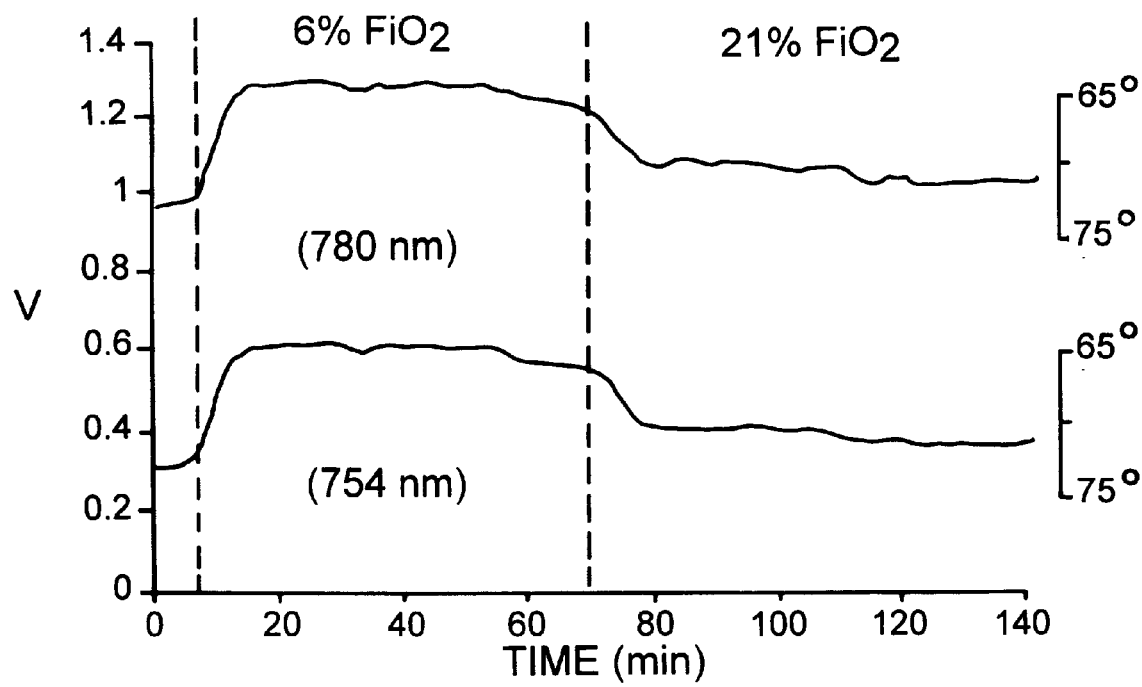
FIGS. 13A and 13B display raw data and calculated saturation data, respectively, measured on a newborn piglet.
Figure 13B:
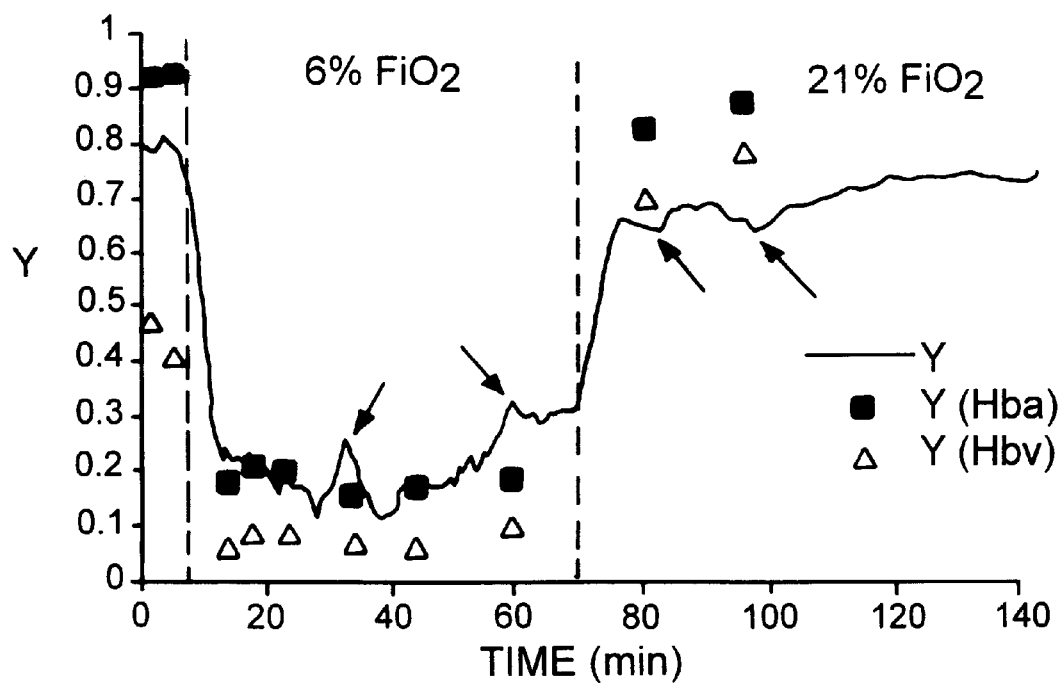

A PMD-3000 system was used to perform the phase modulation measurements. Part of the scull skin was removed and the optical probes were fixed directly to the scull. Typical separations used were 1.7–2 cm. FIGS. 13A and 13B depict the filtered raw data and saturation calculation from a typical measurement. The filtering was done digitally by applying a median filter (kernel size 5) twice followed by a smoothing filter (kernel size 11). The saturation was calculated by numerically solving Eq. 4 for the two wavelengths in order to compute the $\mu_a$ ratio as discussed above. The $\mu_s'$ value for the pigs was selected to be 12 cm$^{-1}$.

During the experimental study, the venous and arterial blood was sampled regularly and blood saturation was immediately calculated. Cerebro-venous saturation values were obtained through an indwelling superior sagittal sinus line and arterial values from a catheter in the femoral artery. The influence of the arterial blood sampling can been seen on FIG. 13B, where the observable sampling points have been marked with arrows, and the local variations are due to the local blood volume changes. The characteristic values of hemoglobin saturation for venous (Hbv) and arterial (Hba) blood are given in FIG. 13B as individual points.

The calculated saturation is somewhat higher than what was expected for the 6% $FiO_2$ interval and lower for the 21% interval. This discrepancy can be correlated by measuring or compensating for water absorption, geometry and scull influence. Furthermore, the extinction coefficients were linearly interpolated for the used wavelengths from charts, and there are random errors introduced in the measurement or derivation of the $\Theta_{instr}^{754}$ and $\Theta_{instr}^{780}$ which may lead to systematic errors in the calculation.

Additional embodiments are within the following claims:

1. An in vivo spectroscopic method for quantifying concentration of an absorptive pigment in biological tissue comprising:

positioning an input port at a selected location relative to the biological tissue;

positioning a detection port at another location spaced at a selected distance of several centimeters from said input port;

generating a first carrier waveform of a selected frequency on the order of $10^8$ Hz;

introducing into the tissue at said input port electromagnetic radiation of at least two selected wavelengths modulated by said carrier waveform, at least one of said wavelengths being sensitive to concentration of said absorptive pigment present in the tissue, said tissue exhibiting a similar scattering property at said wavelengths;

detecting at said detection port the radiation that has migrated over migration paths in a portion of the tissue from said input port, said detected radiation having wavelengths which are the same as said at least two wavelengths introduced to the tissue;

creating a first and a second reference phase signals of predefined substantially different phases;

comparing, at each wavelength, said detected radiation with said first and said second reference signals and determining therefrom a real output signal and an imaginary output signal, at each wavelength, respectively;

providing said scattering property of said portion of the tissue; and quantifying concentration of said absorptive pigment in said portion of said tissue.

2. The spectroscopic method of claim 1 wherein said step of providing said scattering property includes generating a second carrier waveform of a second selected frequency on the order of $10^8$ Hz, said tissue exhibiting similar scattering properties at said selected frequencies; and calculating said phase shift ($\theta$) at said second frequency for each said wavelength.

3. The spectroscopic method of claim 2 wherein said quantifying step includes calculating a ratio of absorption coefficients at said two wavelengths; and calculating a value of oxygen saturation based on said ratio.

4. The spectroscopic method of claim 1 wherein said step of providing said scattering property includes looking up a value of said scattering property from a lookup table that includes said values for different tissue types.

5. The spectroscopic method of claim 4 wherein said value of said scattering property is the effective scattering coefficient $(1-g)\mu_s$.

6. The spectroscopic method of claim 1 wherein said absorptive pigment in an endogenous pigment.

7. The spectroscopic method of claim 6 wherein said endogenous pigment is oxyhemoglobin or deoxyhemoglobin.

8. The spectroscopic method of claim 1 further including calculating, at each wavelength, an amplitude (A) as a square root of a sum of squares of said real output signal and said imaginary output signal.

9. The spectroscopic method of claim 8 wherein said step of providing said scattering property includes calculating said scattering property based on said amplitude (A) at each said wavelength.

10. The spectroscopic method of claim 8 wherein said quantifying step includes employing said calculated amplitude in the following equation:

$$A(\rho, f) = \frac{\left(1 + \psi^2 + 2\psi\cos\frac{\Theta}{2}\right)^{1/2}}{(1+\psi_\infty)} \exp\left(\psi_\infty - \psi\cos\frac{\Theta}{2}\right).$$

11. The spectroscopic method of claim 1 wherein said quantifying step includes calculating, at each wavelength, phase shift ($\theta$) of said detected radiation as the inverse tangent of the ratio of said imaginary output signal and said real output signal.

12. The spectroscopic method of claim 11 wherein said quantifying step includes
    calculating a ratio of absorption coefficients at said two wavelengths; and
    calculating a value of oxygen saturation based on said ratio.

13. The spectroscopic method of claim 12 wherein said step of calculating a ratio of absorption coefficients includes calculating, based on phase shifts calculated at each said wavelength and each said frequency, a ratio of said phase shift and the square root of said frequency.

14. The spectroscopic method of claim 12 wherein said step of calculating a ratio of absorption coefficients includes calculating a ratio of said phase shifts detected at said two wavelengths.

15. The spectroscopic method of claim 14 wherein, at each said wavelength, said phase shift is corrected for $\theta_0$.

16. An in vivo spectroscopic method for quantifying concentration of an absorptive pigment in biological tissue comprising:
    positioning an input port at a selected location relative to the biological tissue;
    positioning a detection port at another location spaced at a selected distance of several centimeters from said input port;
    generating a first carrier waveform of a selected frequency on the order of $10^8$ Hz;
    introducing into the tissue at said input port electromagnetic radiation of at least two selected wavelengths modulated by said carrier waveform, at least one of said wavelengths being sensitive to concentration of said absorptive pigment present in the tissue, said tissue exhibiting a similar scattering property at said wavelengths;
    detecting at said detection port the radiation that has migrated over migration paths in a portion of the tissue from said input port, said detected radiation having wavelengths which are the same as said at least two wavelengths introduced to the tissue;
    comparing, at each said wavelength, the detected radiation with the introduced radiation and measuring therefrom a phase shift ($\theta$) of said detected radiation at each wavelength;
    providing said scattering property of said portion of the tissue; and
    quantifying concentration of said absorptive pigment in said tissue.

17. The spectroscopic method of claim 16 wherein said step of providing said scattering property includes
    changing said selected distance by moving said input port or said detection port to another location; and
    measuring said phase shift at two distances for each said wavelength.

18. The spectroscopic method of claim 16 wherein said absorptive pigment in an exogenous contrast agent.

19. The spectroscopic method of claim 16 wherein said step of providing said scattering property includes looking up a value of said scattering property from a lookup table that includes said values for different tissue types.

20. The spectroscopic method of claim 19 wherein said value of said scattering property is the effective scattering coefficient $(1-g)\mu_s$.

21. The spectroscopic method of claim 16 wherein said step of providing said scattering property includes
    generating a second carrier waveform of a second selected frequency on the order of $10^8$ Hz, said tissue exhibiting similar scattering properties at said selected frequencies; and
    measuring said phase shift at said second frequency for each said wavelength.

22. The spectroscopic method of claim 21 wherein said quantifying step includes
    calculating a ratio of absorption coefficients at said two wavelengths; and
    calculating a value of oxygen saturation based on said ratio.

23. The spectroscopic method of claim 22 wherein said step of calculating a ratio of absorption coefficients includes calculating, based on phase shifts detected at each said wavelength and each said frequency, a ratio of said phase shift and the square root of said frequency.

24. The spectroscopic method of claim 16 wherein said quantifying step includes
    calculating a ratio of absorption coefficients at said two wavelengths; and
    calculating a value of oxygen saturation based on said ratio.

25. The spectroscopic method of claim 24 wherein said step of calculating a ratio of absorption coefficients includes calculating, based on phase shifts detected at each said wavelength and each said frequency, a ratio of said phase shift and the square root of said frequency.

26. The spectroscopic method of claim 24 wherein said step of calculating a ratio of absorption coefficients includes calculating a ratio of said phase shifts detected at said two wavelengths.

27. The spectroscopic method of claim 26 wherein, at each said wavelength, said phase shift is corrected for $\theta_0$.

28. The spectroscopic method of claim 16 further comprising measuring amplitude of said detected radiation.

29. The spectroscopic method of claim 28 wherein said step of providing said scattering property includes calculating said scattering property based on said measured amplitude.

30. The spectroscopic method of claim 28 wherein said quantifying step includes employing the following equation:

$$M(\rho, f) = \frac{\left(1 + \psi^2 + 2\psi\cos\frac{\Theta}{2}\right)^{1/2}}{(1 + \psi_\infty)} \exp\left(\psi_\infty - \psi\cos\frac{\Theta}{2}\right).$$

31. The spectroscopic method of claim 16 wherein said absorptive pigment in an endogenous pigment.

32. The spectroscopic method of claim 31 wherein said endogenous pigment is oxyhemoglobin or deoxyhemoglobin.

33. The spectroscopic method of claim 32 wherein said absorptive pigment in an exogenous contrast agent.

34. A spectroscopic system for quantifying in vivo concentration of an absorptive pigment in biological tissue comprising:
   an oscillator constructed to generate a first carrier waveform of a first frequency on the order of $10^8$ Hz;
   at least one light source, operatively coupled to said oscillator, for generating electromagnetic radiation of at least two selected wavelengths modulated by said carrier waveform, at least one of said wavelengths being sensitive to concentration of said absorptive pigment present in the tissue, said tissue exhibiting a similar scattering property at said wavelengths;
   an input port for introducing said radiation into the tissue;
   a detection port, located several centimeters apart from said input port, for acquiring photons of the radiation that have migrated from said input port over migration paths in a portion of the tissue;
   a detector, optically connected to said detection port, for detecting the radiation having said at least two wavelengths introduced to the tissue, said detector providing to a phase detector a signal corresponding to the detected radiation;
   said phase detector for comparing, at each said wavelength, the detected radiation with the introduced radiation and for determining therefrom the phase shift of said detected radiation at each said wavelength; and
   a processor for receiving said phase shift at each said wavelength and a scattering property of said portion of the tissue and for quantifying therefrom concentration of said absorptive pigment in the tissue.

35. The system of claim 34 wherein said input and detection ports are positionable at several selected relative distances.

36. The system of claim 34 further comprising a magnitude detector constructed to measure an amplitude of said detected radiation.

37. The system of claim 34 wherein said processor calculates said scattering property based on said measured amplitude.

38. The system of claim 34 wherein said processor calculates said concentration by employing the following equation:

$$M(\rho, f) = \frac{\left(1 + \psi^2 + 2\psi\cos\frac{\Theta}{2}\right)^{1/2}}{(1 + \psi_\infty)} \exp\left(\psi_\infty - \psi\cos\frac{\Theta}{2}\right).$$

39. The system of claim 34 wherein said at least one wavelength is sensitive to said absorptive pigment that is an exogenous contrast agent.

40. The system of claim 34 wherein said absorptive pigment is sensitive to an endogenous pigment.

41. The system of claim 40 wherein said at least one wavelength is sensitive to said endogenous pigment that is oxyhemoglobin or deoxyhemoglobin.

42. The system of claim 34 further including a look up table comprising values of said scattering property for different tissue types.

43. The system of claim 42 wherein said value of said scattering property is the effective scattering coefficient, $(1-g)\mu_s$.

44. The system of claim 34 including
   a second oscillator constructed to generate a second carrier waveform of a second selected frequency on the order of $10^8$ Hz, said tissue exhibiting similar scattering properties at said selected frequencies;
   said source operatively coupled to said second oscillator, constructed to generate electromagnetic radiation of said two wavelengths modulated by said second carrier waveform;
   said detector further constructed to detect the radiation modulated by said second carrier waveform;
   said phase detector further constructed to compare, at each said wavelength, the detected radiation of said second carrier waveform with the introduced radiation and determine therefrom the phase shift of said detected radiation; and
   said processor constructed to receive said phase shifts at said second waveform and quantify therefrom the concentration of said absorptive pigment in the tissue.

45. The system of claim 44 wherein said processor is arranged to calculate a ratio of absorption coefficients at said two wavelengths, and calculate a value of oxygen saturation based on said ratio.

$$M(\rho, f) = \frac{\left(1 + \psi^2 + 2\psi\cos\frac{\Theta}{2}\right)^{1/2}}{(1 + \psi_\infty)} \exp\left(\psi_\infty - \psi\cos\frac{\Theta}{2}\right).$$

46. The system of claim 45 wherein said processor is arranged to calculate said ratio of absorption coefficients by taking a ratio of said phase shift and a square root of said frequency for each said wavelength and each said frequency.

47. The system of claim 34 wherein said processor is arranged to calculate a ratio of absorption coefficients at said two wavelengths, and calculate a value of oxygen saturation based on said ratio.

48. The system of claim 47 wherein said processor is arranged to calculate said ratio of absorption coefficients by taking a ratio of said phase shift and a square root of said frequency for each said wavelength.

49. The system of claim 47 wherein said processor is arranged to calculate said ratio of absorption coefficients by taking a ratio of said phase shifts detected at said two wavelengths.

50. The system of claim 49 wherein said processor is arranged to correct said phase shift for $\theta_0$ at each said wavelength.

51. A spectroscopic system for quantifying in vivo concentration of an absorptive pigment in biological tissue comprising:
   an oscillator constructed to generate a first carrier waveform at a selected frequency on the order of $10^8$ Hz;
   at least one light source, operatively coupled to said first oscillator, for generating electromagnetic radiation of at least two selected wavelengths modulated by said carrier waveform, at least one of said wavelengths being sensitive to concentration of said absorptive pigment present in the tissue, said tissue exhibiting a similar scattering property at said wavelengths;

an input port for introducing photons of electromagnetic radiation into the examined biological tissue;

a detection port, spaced several centimeters apart from said input port, for acquiring photons that have migrated over migration paths in an examined portion of the tissue from said input port;

a detector, optically connected to said detection port, for detecting the radiation having said at least two wavelengths introduced to the tissue;

a phase splitter for receiving said carrier waveform and producing first and second reference phase signals of predefined substantially different phases;

first and second double balanced mixers connected to receive from said phase splitter said first and second reference phase signals, respectively, for connecting and receiving from said detector said detector signal, and for producing therefrom a real output signal and an imaginary output signal, respectively; and a processor for receiving said scattering property of said portion of the tissue said real output signal and said imaginary output signal and for quantifying therefrom concentration of said absorptive pigment in said portion of said tissue.

52. The system of claim 51 wherein said processor is further constructed to calculate, at each wavelength, a phase shift (θ) of said detected radiation as the inverse tangent of the ratio of said imaginary output signal and said real output signal.

53. The system of claim 51 wherein said processor is further arranged to calculate, at each wavelength, a detected amplitude (A) as the square root of the sum of the squares of said real output signal and said imaginary output signal.

54. The system of claim 51 wherein said at least one wavelength is sensitive to oxygenation of hemoglobin and wherein said processor is arranged to calculate a ratio of absorption coefficients at said two wavelengths, and calculate a value of oxygen saturation based on said ratio.

55. The system of claim 51 wherein said input and detection ports are positionable at several selected relative distances.

56. The system of claim 51 wherein said at least one said wavelength is sensitive to said absorptive pigment that is an exogenous contrast agent.

57. The system of claim 51 including a second oscillator constructed to generate a second carrier waveform of a second selected frequency on the order of $10^8$ Hz, said tissue exhibiting similar scattering properties at said selected frequencies;

said source operatively coupled to said second oscillator, constructed to generate electromagnetic radiation of said two wavelengths modulated by said second carrier waveform;

said detector further constructed to detect the radiation modulated by said second carrier waveform;

said phase splitter constructed to receive said second carrier waveform and produce first and second reference phase signals of said second frequency and predefined substantially different phases; and first and second double balanced mixers connected to receive from said phase splitter said first and second reference phase signals, respectively, and connected to receive from said detector said detector signal and constructed to produce therefrom a real output signal and an imaginary output signal, respectively, at said second frequency.

58. The system of claim 57 wherein said processor is arranged to calculate said ratio of absorption coefficients by taking a ratio of said phase shift and a square root of said frequency for each said wavelength and each said frequency.

59. The system of claim 51 wherein said processor is arranged to calculate said ratio of absorption coefficients by taking a ratio of said phase shifts detected at said two wavelengths.

60. The system of claim 59 wherein said processor is arranged to correct said phase shift for $\theta_0$, at each said wavelength.

61. The system of claim 51 further including a look up table comprising values of said scattering property for different tissue types.

62. The system of claim 61 wherein said value of said scattering property is the effective scattering coefficient, $(1-g)\mu_s$.

63. The system of claim 51 wherein said at least one said wavelength is sensitive to said absorptive pigment that is an endogenous pigment.

64. The system of claim 63 wherein said at least one said wavelength is sensitive to said endogenous pigment that is oxyhemoglobin or deoxyhemoglobin.

65. The system of claim 51 further comprising a magnitude detector constructed to measure an amplitude of said detected radiation.

66. The system of claim 65 wherein said processor calculates said scattering property based on said measured amplitude.

67. The system of claim 65 wherein said processor calculates said concentration by employing the following equation:

$$A(\rho, f) = \frac{\left(1 + \psi^2 + 2\psi\cos\frac{\Theta}{2}\right)^{1/2}}{(1 + \psi_\infty)} \exp\left(\psi_\infty - \psi\cos\frac{\Theta}{2}\right).$$

* * * * *